US008906879B2

(12) United States Patent
DeMarini et al.

(10) Patent No.: US 8,906,879 B2
(45) Date of Patent: Dec. 9, 2014

(54) COMBINATION FOR THE TREATMENT OF CANCER

(75) Inventors: Douglas J. DeMarini, Collegeville, PA (US); Ngocdiep T. Le, Collegeville, PA (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 13/991,576

(22) PCT Filed: Dec. 20, 2011

(86) PCT No.: PCT/US2011/066017
§ 371 (c)(1),
(2), (4) Date: Jun. 4, 2013

(87) PCT Pub. No.: WO2012/088030
PCT Pub. Date: Jun. 28, 2012

(65) Prior Publication Data
US 2013/0261075 A1    Oct. 3, 2013

Related U.S. Application Data

(60) Provisional application No. 61/424,961, filed on Dec. 20, 2010.

(51) Int. Cl.
*A01N 43/04*     (2006.01)
*A61K 31/70*     (2006.01)
*A61K 31/519*    (2006.01)
*A61K 9/20*      (2006.01)
*A61K 9/48*      (2006.01)
*A61K 31/7068*   (2006.01)
*A61K 9/00*      (2006.01)

(52) U.S. Cl.
CPC .......... *A61K 31/7068* (2013.01); *A61K 31/519* (2013.01); *A61K 9/2018* (2013.01); *A61K 9/4858* (2013.01); *A61K 9/0019* (2013.01); *A61K 9/2054* (2013.01)

USPC .............................................. 514/49; 514/43

(58) Field of Classification Search
None
See application file for complete search history.

(56) References Cited

U.S. PATENT DOCUMENTS

| 6,001,994 A | 12/1999 | Weigel |
| 7,378,423 B2 | 5/2008 | Kawasaki et al. |
| 2006/0014768 A1 | 1/2006 | Kawasaki et al. |
| 2009/0004200 A1 | 1/2009 | Gevas et al. |

FOREIGN PATENT DOCUMENTS

WO    WO2005/121142    12/2005

OTHER PUBLICATIONS

Allen, et al., *Semin. Oncol.*, 30(5 Suppl. 16):105-116 (2003).
Berenbaum, et al., *Adv. Cancer Research*, 35:269-335 (1981).
Chou, et al., *Adv. Enzyme Regul.*, 22:27-55 (1984).
Crews, et al., *Cell*, 74:215-217 (1993).
Davies, et al., *Nature*, 417:949-954 (2002).
Hodges, et al.,*Eukaryon*, 6:68-69 (2010).
Liu, et al., *Mol. Cancer Ther.*, 10(3):518-530 (2011).
*The Journal of Biological Chemistry*, 276(4):2686-2692 (2001).

*Primary Examiner* — Patrick Lewis
(74) *Attorney, Agent, or Firm* — Wayne J. Dustman; Edward R. Gimmi

(57) ABSTRACT

The present invention relates to a method of treating cancer in a human and to pharmaceutical combinations useful in such treatment. In particular, the method relates to a cancer treatment method that includes administering 4-amino-1-(2-deoxy-2,2-difluoro-β-D-erythro-pentofuranosyl)pyrimidin-2(1H)-on 2', 2'-difluoro-2'-deoxycytidine, or a pharmaceutically acceptable salt thereof, and N-{3-[3-cyclopropyl-5-(2-fluoro-4-iodo-phenylamino)6,8-dimethy; -2,4,7-trioxo-3,4,6,7-tetrahydro-2H-pyrido[4,3-d]pyrimidin-1-yl]phenyl}acetamide, or a pharmaceutically acceptable salt or solvate thereof, to a human in need thereof.

10 Claims, 1 Drawing Sheet

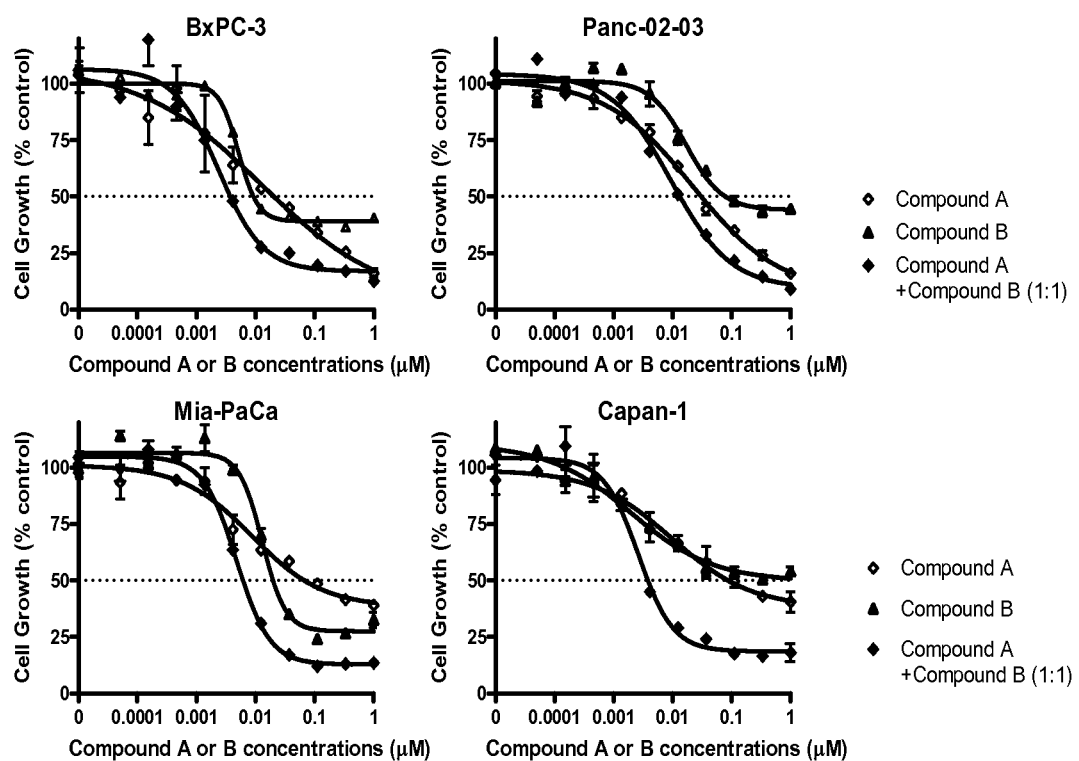

COMBINATION FOR THE TREATMENT OF CANCER

This application is a 371 of International Application No. PCT/US2011/066017, filed 20 Dec. 2011, which claims the benefit of U.S. Provisional Application No. 61/424961 filed 20 Dec. 2010.

FIELD OF THE INVENTION

The present invention relates to a method of treating cancer in a mammal and to combinations useful in such treatment. In particular, the method relates to a novel combination comprising the antimetabolite nucleoside: 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt thereof, and MEK inhibitor: N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, pharmaceutical compositions comprising the same, and methods of using such combinations in the treatment of cancer.

BACKGROUND OF THE INVENTION

Generally, cancer results from the deregulation of the normal processes that control cell division, differentiation and apoptotic cell death. Apoptosis (programmed cell death) plays essential roles in embryonic development and pathogenesis of various diseases, such as degenerative neuronal diseases, cardiovascular diseases and cancer. One of the most commonly studied pathways, which involves kinase regulation of apoptosis, is cellular signaling from growth factor receptors at the cell surface to the nucleus (Crews and Erikson, Cell, 74:215-17, 1993).

Nucleosides are glycosylamines consisting of a nucleobase (often referred to as simply base) bound to a ribose or deoxyribose sugar via a beta-glycosidic linkage. Examples of nucleosides include cytidine, uridine, adenosine, guanosine, thymidine and inosine.

Nucleosides can be phosphorylated by specific kinases in the cell on the sugar's primary alcohol group (—$CH_2$—OH), producing nucleotides, which are the molecular building-blocks of DNA and RNA.

Nucleosides can be produced by de novo synthesis pathways, in particular in the liver, but they are more abundantly supplied via ingestion and digestion of nucleic acids in the diet, whereby nucleotidases break down nucleotides (such as the thymine nucleotide) into nucleosides (such as thymidine) and phosphate. The nucleosides, in turn, are subsequently broken down in the lumen of the digestive system by nucleosidases into nucleobases and ribose or deoxyribose.

In addition, nucleotides can be broken down inside the cell into nitrogenous bases, and ribose-1-phosphate or deoxyribose-1-phosphate.

In medicine several nucleoside analogues are used as antiviral or anticancer agents. The viral polymerase incorporates these compounds with non-canonical bases. These compounds are activated in the cells by being converted into nucleotides, they are administered as nucleosides since charged nucleotides cannot easily cross cell membranes.

Mitogen-activated protein (MAP) Kinase/extracellular signal-regulated kinase (ERK) kinase (hereinafter referred to as MEK) is known to be involved in the regulation of numerous cellular processes. The Raf family (B-Raf, C-Raf etc.) activates the MEK family (MEK-1, MEK-2 etc.) and the MEK family activates the ERK family (ERK-1 and ERK-2). Broadly, the signaling activity of the RAF/MEK/ERK pathway controls mRNA translation. This includes genes related to the cell cycle. Hence, hyperactivation of this pathway can lead to uncontrolled cell proliferation. Deregulation of the RAF/MEK/ERK pathway by ERK hyperactivation is seen in approximately 30% of all human malignancies (Allen, L F, et al., Semin. Oncol. 2003. 30(5 Suppl 16):105-16). RAS, which can signal through both the PI3K/AKT and RAF/MEK/ERK, has a mutated oncogenic protein in 15% of all cancers (Davies, H. et al. Nature. 2002. 417:949-54). Also, activating BRAF mutations have been identified at a high frequency in specific tumor types (e.g., melanomas) (Davies, H. et al. Nature. 2002. 417:949-54). Although activating mutations in MEK itself don't appear to frequently occur in human cancers, MEK is thought to be an important drug target for treating human cancer because of its central role in the ERK pathway. Further, MEK inhibitory activity effectively induces inhibition of ERK1/2 activity and suppression of cell proliferation (The Journal of Biological Chemistry, vol. 276, No. 4, pp. 2686-2692, 2001), and the compound is expected to show effects on diseases caused by undesirable cell proliferation, such as tumor genesis and/or cancer.

It would be useful to provide a improved therapy which provides more effective and/or enhanced treatment of an individual suffering the effects of cancer.

SUMMARY OF THE INVENTION

One embodiment of this invention provides a combination comprising:

(i) a compound of Structure (I):

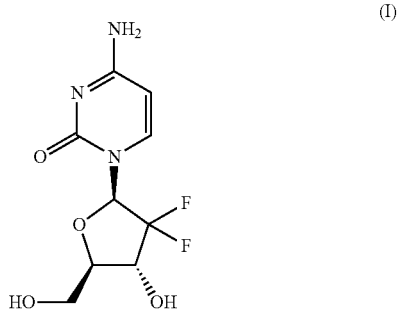 [SMILES: Nc1ccn([C@@H]2O[C@H](CO)[C@@H](O)C2(F)F)c(=O)n1]

(I)

or a pharmaceutically acceptable salt thereof; and (ii) a compound of Structure (II):

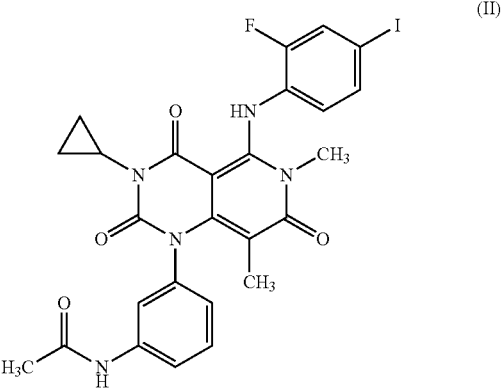 [SMILES: CC(=O)Nc1cccc(-n2c(=O)n(C3CC3)c(=O)c3c(Nc4ccc(I)cc4F)n(C)c(=O)c(C)c32)c1]

(II)

or a pharmaceutically acceptable salt or solvate thereof.

One embodiment of this invention provides a method of treating cancer in a human in need thereof which comprises the in vivo administration of a therapeutically effective amount of a combination of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, to such human.

One embodiment of this invention provides a method of treating cancer in a human in need thereof which comprises the in vivo administration of a therapeutically effective amount of a combination of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, to such human, wherein the combination is administered within a specified period, and wherein the combination is administered for a duration of time.

One embodiment of this invention provides a method of treating cancer in a human in need thereof which comprises the in vivo administration of a therapeutically effective amount of a combination of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, to such human, wherein the compounds of the combination are administered sequentially.

BRIEF DESCRIPTION OF THE DRAWINGS

FIG. 1 depicts cell growth inhibition by N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide and gemcitabine, alone and in combination, for BxPC-3, Panc-02-03, Mia-PaCa and Capan-1 human pancreatic cancer cells.

DETAILED DESCRIPTION OF THE INVENTION

The present invention relates to combinations that exhibit antiproliferative activity. Suitably, the method relates to methods of treating cancer by the co-administration of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, (hereinafter Compound A, or a pharmaceutically acceptable salt, suitably the hydrochloride salt, thereof, which compound is represented by Structure I:

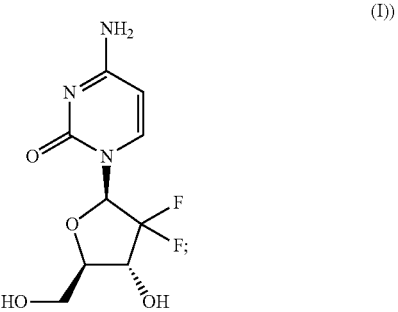 [SMILES: Nc1ccn([C@@H]2O[C@H](CO)[C@@H](O)C2(F)F)c(=O)n1]

and N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate; suitably the dimethyl sulfoxide solvate, thereof, (hereinafter Compound B or a pharmaceutically acceptable salt or solvate, suitably the dimethyl sulfoxide solvate, thereof, which compound is represented by Structure II:

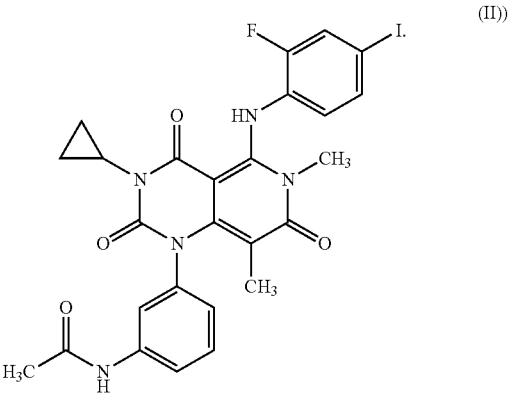 [SMILES: CC(=O)Nc1cccc(-n2c(=O)n(C3CC3)c(=O)c3c(Nc4ccc(I)cc4F)n(C)c(=O)c(C)c32)c1]

Compound A is known anti-neoplastic compound marketed under the generic name gemcitabine. Gemcitabine can be prepared as described in U.S. Pat. No. 6,001,994, which issued on Dec. 14, 1999.

Suitably, Compound A is in the form of a hydrochloride salt. Gemcitabine hydrochloride is marketed under the trade name Gemzar® and can be prepared by one of skill in the art from the description in U.S. Pat. No. 6,001,994, which issued on Dec. 14, 1999.

Compound B is disclosed and claimed, along with pharmaceutically acceptable salts and solvates thereof, as being useful as an inhibitor of MEK activity, particularly in treatment of cancer, in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference, Compound B is the compound of Example 4-1. Compound B can be prepared as described in International Application No. PCT/JP2005/011082. Compound B can be prepared as described in United States Patent Publication No. US 2006/0014768, Published Jan. 19, 2006, the entire disclosure of which is hereby incorporated by reference.

Suitably, Compound B is in the form of a dimethyl sulfoxide solvate. Suitably, Compound B is in the form of a sodium salt. Suitably, Compound B is in the form of a solvate selected from: hydrate, acetic acid, ethanol, nitromethane, chlorobenzene, 1-pentanci, isopropyl alcohol, ethylene glycol and 3-methyl-1-butanol. These solvates and salt forms can be prepared by one of skill in the art from the description in International Application No. PCT/JP2005/011082 or United States Patent Publication No. US 2006/0014768.

The administration of a therapeutically effective amount of the combinations of the invention are advantageous over the individual component compounds in that the combinations provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the component compounds.

The compounds of the invention may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of Compound A, and pharmaceutically acceptable salts thereof, and Compound B, and pharmaceutically acceptable salts or solvates thereof.

The compounds of the invention may form a solvate which is understood to be a complex of variable stoichiometry formed by a solute (in this invention, Compound A or a salt thereof and/or Compound B or a salt thereof) and a solvent. Such solvents for the purpose of the invention may not interfere with the biological activity of the solute. Examples of suitable solvents include, but are not limited to, water, methanol, dimethyl sulfoxide, ethanol and acetic acid. Suitably the solvent used is a pharmaceutically acceptable solvent. Suitably the solvent used is water or dimethyl sulfoxide.

The pharmaceutically acceptable salts of the compounds of the invention are readily prepared by those of skill in the art.

Also, contemplated herein is a method of treating cancer using a combination of the invention where Compound A, or a pharmaceutically acceptable salt thereof, and/or Compound B or a pharmaceutically acceptable salt or solvate thereof are administered as pro-drugs. Pharmaceutically acceptable pro-drugs of the compounds of the invention are readily prepared by those of skill in the art.

When referring to a dosing protocol, the term "day", "per day" and the like, refer to a time within one calendar day which begins at midnight and ends at the following midnight.

By the term "treating" and derivatives thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

By the term "combination" and derivatives thereof, unless otherwise defined, as used herein is meant either, simultaneous administration or any manner of separate sequential administration of a therapeutically effective amount of Compound A, or a pharmaceutically acceptable salt thereof, and Compound B or a pharmaceutically acceptable salt or solvate thereof. Preferably, if the administration is not simultaneous, the compounds are administered in a close time proximity to each other. Furthermore, it does not matter if the compounds are administered in the same dosage form, e.g. one compound may be administered topically and the other compound may be administered orally. Suitably, Compound A is administered by IV and Compound B is administered orally.

By the term "combination kit" as used herein is meant the pharmaceutical composition or compositions that are used to administer Compound A, or a pharmaceutically acceptable salt thereof, and Compound B, or a pharmaceutically acceptable salt or solvate thereof, according to the invention. When both compounds are administered simultaneously, the combination kit can contain Compound A, or a pharmaceutically acceptable salt thereof, and Compound B, or a pharmaceutically acceptable salt or solvate thereof, in a single pharmaceutical composition, such as a tablet, or in separate pharmaceutical compositions. When the compounds are not administered simultaneously, the combination kit will contain Compound A, or a pharmaceutically acceptable salt thereof, and Compound B, or a pharmaceutically acceptable salt or solvate thereof, in separate pharmaceutical compositions. The combination kit can comprise Compound A, or a pharmaceutically acceptable salt thereof, and Compound B, or a pharmaceutically acceptable salt or solvate thereof, in separate pharmaceutical compositions in a single package or in separate pharmaceutical compositions in separate packages.

In one aspect there is provided a combination kit comprising the components:

Compound A, or a pharmaceutically acceptable salt thereof, in association with a pharmaceutically acceptable carrier; and Compound B, or a pharmaceutically acceptable salt or solvate thereof, in association with a pharmaceutically acceptable carrier.

In one embodiment of the invention the combination kit comprises the following components:

Compound A, or a pharmaceutically acceptable salt thereof, in association with a pharmaceutically acceptable carrier; and Compound B, or a pharmaceutically acceptable salt or solvate thereof, in association with a pharmaceutically acceptable carrier, wherein the components are provided in a form which is suitable for sequential, separate and/or simultaneous administration.

In one embodiment the combination kit comprises:

a first container comprising Compound A, or a pharmaceutically acceptable salt thereof, in association with a pharmaceutically acceptable carrier; and a second container comprising Compound B, or a pharmaceutically acceptable salt or solvate thereof, in association with a pharmaceutically acceptable carrier, and a container means for containing said first and second containers.

The "combination kit" can also be provided by instruction, such as dosage and administration instructions. Such dosage and administration instructions can be of the kind that is provided to a doctor, for example by a drug product label, or they can be of the kind that is provided by a doctor, such as instructions to a patient.

As used herein the term "Compound $A^2$" means—Compound A, or a pharmaceutically acceptable salt thereof—.

As used herein the term "Compound $B^2$" means—Compound B, or a pharmaceutically acceptable salt or solvate thereof—.

Suitably the combinations of this invention are administered within a "specified period".

By the term "specified period" and derivatives thereof, as used herein is meant the interval of time between the administration of one of Compound $A^2$ and Compound $B^2$ and the other of Compound $A^2$ and Compound $B^2$. Unless otherwise defined, the specified period can include simultaneous administration. When both compounds of the invention are administered once a day the specified period refers to timing of the administration of Compound $A^2$ and Compound $B^2$ during a single day. When one or both compounds of the invention are administered more than once a day, the specified period is calculated based on the first administration of each compound on a specific day. All administrations of a compound of the invention that are subsequent to the first during a specific day are not considered when calculating the specific period.

Suitably, if the compounds are administered within a "specified period" and not administered simultaneously, they are both administered within about 24 hours of each other—in this case, the specified period will be about 24 hours; suitably they will both be administered within about 12 hours of each other—in this case, the specified period will be about 12 hours; suitably they will both be administered within about 11 hours of each other—in this case, the specified period will be about 11 hours; suitably they will both be administered within about 10 hours of each other—in this case, the specified period will be about 10 hours; suitably they will both be administered within about 9 hours of each other—in this case, the specified period will be about 9 hours; suitably they will both be administered within about 8 hours of each other—in this case, the specified period will be about 8 hours; suitably they will both be administered within about 7 hours of each other—in this case, the specified period will be about 7 hours; suitably they will both be administered within about 6 hours of each other—in this case, the specified period will be about 6 hours; suitably they will both be administered within about 5 hours of each other—in this case, the specified period will be about 5 hours; suitably they will both be administered within about 4 hours of each other—in this case, the specified period will be about 4 hours; suitably they will both be administered within about 3 hours of each other—in this case, the specified period will be about 3 hours; suitably they will be administered within about 2 hours of each other—in this case, the specified period will be about 2 hours; suitably they will both be administered within about 1 hour of each other—in this case, the specified period will be about 1 hour. As used herein, the administration of Compound $A^2$ and Compound $B^2$ in less than about 45 minutes apart is considered simultaneous administration.

Suitably, when the combination of the invention is administered for a "specified period", the compounds will be co-administered for a "duration of time".

By the term "duration of time" and derivatives thereof, as used herein is meant that both compounds of the invention are administered within a "specified period" for an indicated number of consecutive days, optionally followed by a number of consecutive days where only one of the component compounds is administered. Unless otherwise defined, the "duration of time" and in all dosing protocols described herein, do not have to commence with the start of treatment and terminate with the end of treatment, it is only required that the number of consecutive days in which both compounds are administered and the optional number of consecutive days in which only one of the component compounds is administered, or the indicated dosing protocol, occur at some point during the course of treatment.

Regarding "specified period" administration:

Suitably, during the course of treatment, both compounds will be administered within a specified period for at least 1 day—in this case, the duration of time will be at least 1 day; suitably, during the course of treatment, both compounds will be administered within a specified period for at least 2 consecutive days—in this case, the duration of time will be at least 2 days; suitably, during the course of treatment, both compounds will be administered within a specified period for at least 3 consecutive days—in this case, the duration of time will be at least 3 days; suitably, during the course of treatment, both compounds will be administered within a specified period for at least 5 consecutive days—in this case, the duration of time will be at least 5 days; suitably, during the course of treatment, both compounds will be administered within a specified period for at least 7 consecutive days—in this case, the duration of time will be at least 7 days; suitably, during the course of treatment, both compounds will be administered within a specified period for at least 14 consecutive days—in this case, the duration of time will be at least 14 days; suitably, during the course of treatment, both compounds will be administered within a specified period for at least 30 consecutive days—in this case, the duration of time will be at least 30 days. When, during the course of treatment, both compounds are administered within a specified period for over 30 days, the treatment is considered chronic treatment and will continue until an altering event, such as a reassessment in cancer status or a change in the condition of the patient, warrants a modification to the protocol.

Further regarding "specified period" administration:

Suitably, during the course of treatment, both compounds will be administered within a specified period for at least 1 day, followed by the administration of Compound $A^2$ alone for at least 1 day—in this case, the duration of time will be at least 2 days; suitably, during the course of treatment, both compounds will be administered within a specified period for at least 1 day, followed by administration of Compound $A^2$ alone for at least 2 days—in this case, the duration of time will be at least 3 days; suitably, during the course of treatment, both compounds will be administered within a specified period for at least 1 day, followed by administration of Compound $A^2$ alone for at least 3 days —in this case, the duration of time will be at least 4 days; suitably, during the course of treatment, both compounds will be administered within a specified period for at least 1 day, followed by administration of Compound $A^2$ alone for at least 4 days—in this case, the duration of time will be at least 5 days; suitably, during the course of treatment, both compounds will be administered within a specified period for at least 1 day, followed by administration of Compound $A^2$ alone for at least 5 days—in this case, the duration of time will be at least 6 days; suitably, during the course of treatment, both compounds will be administered within a specified period for at least 1 day, followed by administration of Compound $A^2$ alone for at least 6 days—in this case, the duration of time will be at least 7 days; suitably, during the course of treatment, both compounds will be administered within a specified period for at least 1 day, followed by administration of Compound $A^2$ alone for at least 7 days—in this case, the duration of time will be at least 8 days; suitably, during the course of treatment, both compounds will be administered within a specified period for at least 2 consecutive days, followed by administration of Compound $A^2$ alone for at least 1 day—in this case, the duration of time will be at least 3 days; suitably, during the course of treatment, both compounds will be administered within a specified period for at least 2 consecutive days, followed by administration of Compound $A^2$ alone for at least 2 consecutive days—in this case, the duration of time will be at least 4 days; suitably, during the course of treatment, both compounds will be administered within a specified period for at least 2 consecutive days, followed by administration of Compound $A^2$ alone for at least 3 consecutive days —in this case, the duration of time will be at least 5 days; suitably, during the course of treatment, both compounds will be administered within a specified period for at least 2 consecutive days, followed by administration of Compound $A^2$ alone for at least 4 consecutive days—in this case, the duration of time will be at least 6 days; suitably, during the course of treatment, both compounds will be administered within a specified period for at least 2 consecutive days, followed by administration of Compound $A^2$ alone for at least 5 consecutive days—in this case, the duration of time will be at least 7 days; suitably, during the course of treatment, both compounds will be administered within a specified period for at least 2 consecutive days, followed by administration of Compound $A^2$ alone for at least 6 consecutive days—in this case, the duration of time will be at least 8 days; suitably, during the course of treatment, both compounds will be administered within a specified period for at least 2 consecutive days, followed by administration of Compound $A^2$ alone for at least 7 consecutive days—in this case, the duration of time will be at least 9 days; suitably, during the course of treatment, both compounds will be administered within a specified period for at least 3 consecutive days, followed by administration of Compound $A^2$ alone for at least 1 day—in this case, the duration of time will be at least 4 days; suitably, during the course of treatment, both compounds will be administered within a specified period for at least 3 consecutive days, followed by administration of Compound $A^2$ alone for at least 2 consecutive days —in this case, the duration of time will be at least 5 days; suitably, during the course of treatment, both compounds will be administered within a specified period for at least 3 consecutive days, followed by administration of Compound $A^2$ alone for at least 3 consecutive days—in this case, the duration of time will be at least 6 days; suitably, during the course of treatment, both compounds will be administered within a specified period for at least 3 consecutive days, followed by administration of Compound $A^2$ alone for at least 4 consecutive days—in this case, the duration of time will be at least 7 days; suitably, during the course of treatment, both compounds will be administered within a specified period for at least 3 consecutive days, followed by administration of Compound $A^2$ alone for at least 5 consecutive days—in this case, the duration of time will be at least 8 days; suitably, during the course of treatment, both compounds will be administered within a specified period for at least 3 consecutive days, followed by administration of Compound $A^2$ alone for at least 6 consecutive days—in this case, the duration of time will be at least 9 days; suitably, during the course of treatment, both compounds will be administered within a specified period for at least 3 consecutive days, followed by administration of Compound $A^2$ alone for at least 7 consecutive days —in this case, the duration of time will be at least 10 days; suitably, during the course of treatment, both compounds will be administered within a specified period for at least 4 consecutive days, followed by administration of Compound $A^2$ alone for at least 1 day—in this case, the duration of time will be at least 5 consecutive days; suitably, during the course of treatment, both compounds will be administered within a specified period for at least 4 consecutive days, followed by administration of Compound $A^2$ alone for at least 2 consecutive days—in this case, the duration of time will be at least 6 consecutive days; suitably, during the course of treatment, both compounds will be administered within a specified period for at least 4 consecutive days, followed by administration of Compound $A^2$ alone for at least 3 consecutive days—in this case, the duration of time will be at least 7 consecutive days; suitably, during the course of treatment, both compounds will be administered within a specified period for at least 4 consecutive days, followed by administration of Compound $A^2$ alone for at least 4 consecutive days—in this case, the duration of time will be at least 8 consecutive days; suitably, during the course of treatment, both compounds will be administered within a specified period for at least 4 consecutive days, followed by administration of Compound $A^2$ alone for at least 7 consecutive days—in this case, the duration of time will be at least 11 consecutive days; suitably, during the course of treatment, both compounds will be administered within a specified period for at least 5 consecutive days, followed by administration of Compound $A^2$ alone for at least 1 day—in this case, the duration of time will be at least 6 consecutive days; suitably, during the course of treatment, both compounds will be administered within a specified period for at least 5 consecutive days, followed by administration of Compound $A^2$ alone for at least 2 consecutive days—in this case, the duration of time will be at least 7 consecutive days; suitably, during the course of treatment, both compounds will be administered within a specified period for at least 5 consecutive days, followed by administration of Compound $A^2$ alone for at least 3 consecutive days—in this case, the duration of time will be at least 8 consecutive days; suitably, during the course of treatment, both compounds will be administered within a specified period for at least 5 consecutive days, followed by administration of Compound $A^2$ alone for at least 4 consecutive days —in this case, the duration of time will be at least 9 consecutive days; suitably, during the course of treatment, both compounds will be administered within a specified period for at least 5 consecutive days, followed by administration of Compound $A^2$ alone for at least 5 consecutive days—in this case, the duration of time will be at least 10 consecutive days; suitably, during the course of treatment, both compounds will be administered within a specified period for at least 7 consecutive days, followed by administration of Compound $A^2$ alone for at least 2 consecutive days—in this case, the duration of time will be at least 9 consecutive days; suitably, during the course of treatment, both compounds will be administered within a specified period for at least 14 consecutive days, followed by administration of Compound $A^2$ alone for at least 7 consecutive days—in this case, the duration of time will be at least 21 consecutive days; suitably, during the course of treatment, both compounds will be administered within a specified period for at least 30 consecutive days, followed by administration of Compound $A^2$ alone for at least 7 consecutive days—in this case, the duration of time will be at least 37 consecutive days. Suitably, during the course of treatment, both compounds will be administered within a specified period for from 1 to 3 consecutive days, followed by administration of Compound $A^2$ alone for from 3 to 7 consecutive days. Suitably, during the course of treatment, both compounds will be administered within a specified period for from 3 to 6 consecutive days, followed by administration of Compound $A^2$ alone for from 1 to 4 consecutive days. Suitably, during the course of treatment, both compounds will be administered within a specified period for 5 consecutive days, followed by administration of Compound $A^2$ alone for 2 consecutive days. Suitably, during the course of treatment, both compounds will be administered within a specified period for 2 consecutive days, followed by administration of Compound $A^2$ alone for from 3 to 7 consecutive days. Suitably, during the course of treatment, both compounds will be administered within a specified period for from 1 to 3 days over a 7 day period, and during the other days of the 7 day period Compound $A^2$ will be administered alone. Suitably, during the course of treatment, both compounds will be administered within a specified period for 2 days over a 7 day period, and during the other days of the 7 day period Compound $A^2$ will be administered alone.

Suitably, if the compounds are not administered during a "specified period", they are administered sequentially. By the term "sequential administration", and derivates thereof, as used herein is meant that one of Compound $A^2$ and Compound $B^2$ is administered for 1 or more consecutive days and the other of Compound $A^2$ and Compound $B^2$ is subsequently administered for 1 or more consecutive days. Unless otherwise defined, the "sequential administration" and in all dosing protocols described herein, do not have to commence with the start of treatment and terminate with the end of treatment, it is only required that the administration of one of Compound $A^2$ and Compound $B^2$ followed by the administration of the other of Compound $A^2$ and Compound $B^2$, or the indicated dosing protocol, occur at some point during the course of treatment. Also, contemplated herein is a drug holiday utilized between the sequential administration of one of Compound $A^2$ and Compound $B^2$ and the other of Compound $A^2$ and Compound $B^2$. As used herein, a drug holiday is a period of days after the sequential administration of one of Compound $A^2$ and Compound $B^2$ and before the administration of the other of Compound $A^2$ and Compound $B^2$ where neither Compound $A^2$ nor Compound $B^2$ is administered. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Regarding sequential administration:

Suitably, one of Compound $A^2$ and Compound $B^2$ is administered for from 1 to 30 consecutive days, followed by an optional drug holiday, followed by administration of the other of Compound $A^2$ and Compound $B^2$ for from 1 to 30 consecutive days. Suitably, one of Compound $A^2$ and Compound $B^2$ is administered for from 1 to 21 consecutive days, followed by an optional drug holiday, followed by administration of the other of Compound $A^2$ and Compound $B^2$ for from 1 to 21 consecutive days. Suitably, one of Compound $A^2$ and Compound $B^2$ is administered for from 1 to 14 consecutive days, followed by a drug holiday of from 1 to 14 days, followed by administration of the other of Compound $A^2$ and Compound $B^2$ for from 1 to 14 consecutive days. Suitably, one of Compound $A^2$ and Compound $B^2$ is administered for from 2 to 7 consecutive days, followed by a drug holiday of from 2 to 10 days, followed by administration of the other of Compound $A^2$ and Compound $B^2$ for from 2 to 7 consecutive days.

Suitably, Compound $B^2$ will be administered first in the sequence, followed by an optional drug holiday, followed by administration of Compound $A^2$. Suitably, Compound $B^2$ is administered for from 1 to 21 consecutive days, followed by an optional drug holiday, followed by administration of Compound $A^2$ for from 1 to 21 consecutive days. Suitably, Compound $B^2$ is administered for from 3 to 21 consecutive days, followed by a drug holiday of from 1 to 14 days, followed by administration of Compound $A^2$ for from 3 to 21 consecutive days. Suitably, Compound $B^2$ is administered for from 3 to 21 consecutive days, followed by a drug holiday of from 3 to 14 days, followed by administration of Compound $A^2$ for from 3 to 21 consecutive days. Suitably, Compound $B^2$ is administered for 21 consecutive days, followed by an optional drug holiday, followed by administration of Compound $A^2$ for 14 consecutive days. Suitably, Compound $B^2$ is administered for 14 consecutive days, followed by a drug holiday of from 1 to 14 days, followed by administration of Compound $A^2$ for 14 consecutive days. Suitably, Compound $B^2$ is administered for 7 consecutive days, followed by a drug holiday of from 3 to 10 days, followed by administration of Compound $A^2$ for 7 consecutive days. Suitably, Compound $B^2$ is administered for 3 consecutive days, followed by a drug holiday of from 3 to 14 days, followed by administration of Compound $A^2$ for 7 consecutive days. Suitably, Compound $B^2$ is administered for 3 consecutive days, followed by a drug holiday of from 3 to 10 days, followed by administration of Compound $A^2$ for 3 consecutive days.

Suitably, Compound $A^2$ will be administered first in the sequence, followed by an optional drug holiday, followed by administration of Compound $B^2$. Suitably, Compound $A^2$ is administered for from 1 to 21 consecutive days, followed by an optional drug holiday, followed by administration of Compound $B^2$ for from 1 to 21 consecutive days. Suitably, Compound $A^2$ is administered for from 3 to 21 consecutive days, followed by a drug holiday of from 1 to 14 days, followed by administration of Compound $B^2$ for from 3 to 21 consecutive days. Suitably, Compound $A^2$ is administered for from 3 to 21 consecutive days, followed by a drug holiday of from 3 to 14 days, followed by administration of Compound $B^2$ for from 3 to 21 consecutive days. Suitably, Compound $A^2$ is administered for 21 consecutive days, followed by an optional drug holiday, followed by administration of Compound $B^2$ for 14 consecutive days. Suitably, Compound $A^2$ is administered for 14 consecutive days, followed by a drug holiday of from 1 to 14 days, followed by administration of Compound $B^2$ for 14 consecutive days. Suitably, Compound $A^2$ is administered for 7 consecutive days, followed by a drug holiday of from 3 to 10 days, followed by administration of Compound $B^2$ for 7 consecutive days. Suitably, Compound $A^2$ is administered for 3 consecutive days, followed by a drug holiday of from 3 to 14 days, followed by administration of Compound $B^2$ for 7 consecutive days. Suitably, Compound $A^2$ is administered for 3 consecutive days, followed by a drug holiday of from 3 to 10 days, followed by administration of Compound $B^2$ for 3 consecutive days. Suitably, Compound $A^2$ is administered for 7 consecutive days, followed by administration of Compound $B^2$ for 1 day. Suitably, Compound $A^2$ is administered for 6 consecutive days, followed by administration of Compound $B^2$ for 1 day. Suitably, Compound $B^2$ is administered for 1 day, followed by administration of Compound $A^2$ for 7 consecutive days. Suitably, Compound $B^2$ is administered for 1 day, followed by administration of Compound $A^2$ for 6 consecutive days.

It is understood that a "specified period" administration and a "sequential" administration can be followed by repeat dosing or can be followed by an alternate dosing protocol, and a drug holiday may precede the repeat dosing or alternate dosing protocol.

Suitably, the dosing protocol will be:
Compound A administered in:
  a first cycle consisting of 1000 mg/m2 intravenous infusion over 30 minutes weekly for 7 weeks followed by one week of no treatment with Compound A,
  with
  subsequent cycles consisting of 1000 mg/m2 intravenous infusion over 30 minutes on days 1, 8, and 15 followed by 1 week of no treatment with Compound A for each 28-day treatment period; and
Compound B administered in:
  a daily dose selected from: about 0.5 mg, about 1 mg and about 2 mg, suitably about 2 mg, by weight of the free or unsalted and un-solvated compound.

Suitably, the amount of Compound $B^2$ administered as part of the combination according to the present invention will be an amount selected from about 0.125 mg to about 10 mg; suitably, the amount will be selected from about 0.25 mg to about 9 mg; suitably, the amount will be selected from about 0.25 mg to about 8 mg; suitably, the amount will be selected from about 0.5 mg to about 8 mg; suitably, the amount will be selected from about 0.5 mg to about 7 mg; suitably, the amount will be selected from about 1 mg to about 7 mg; suitably, the amount will be about 5 mg. Accordingly, the amount of Compound $B^2$ administered as part of the combination according to the present invention will be an amount selected from about 0.125 mg to about 10 mg. For example, the amount of Compound $B^2$ administered as part of the combination according to the present invention can be 0.125 mg, 0.25 mg, 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg.

As used herein, all amounts specified for Compound $A^2$ and Compound $B^2$ are indicated as the administered amount of free or unsalted compound per dose.

The method of the present invention may also be employed with other therapeutic methods of cancer treatment.

While it is possible that, for use in therapy, therapeutically effective amounts of the combinations of the present invention may be administered as the raw chemical, it is preferable to present the combinations as a pharmaceutical composition or compositions. Accordingly, the invention further provides pharmaceutical compositions, which include Compound $A^2$ and/or Compound $B^2$, and one or more pharmaceutically acceptable carriers. The combinations of the present invention are as described above. The carrier(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical formulation including admixing Compound $A^2$ and/or Compound $B^2$ with one or more pharmaceutically acceptable carriers. As indicated above, such elements of the pharmaceutical combination utilized may be presented in separate pharmaceutical compositions or formulated together in one pharmaceutical formulation.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

Compound $A^2$ and Compound $B^2$ may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that Compound $A^2$ and Compound $B^2$ may be compounded together in a pharmaceutical composition/formulation. Suitably, Compound $A^2$ and Compound $B^2$ are administered in separate pharmaceutical compositions.

The compounds or combinations of the current invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include a prolonged release material, such as glyceryl monostearate or glyceryl distearate, alone or with a wax. The amount of solid carrier varies widely but, suitably, may be from about 25 mg to about 1 g per dosage unit. When a liquid carrier is used, the preparation will suitably be in the form of a syrup, elixir, emulsion, soft gelatin capsule, sterile injectable liquid such as an ampoule, or an aqueous or nonaqueous liquid suspension.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

It should be understood that in addition to the ingredients mentioned above, the formulations may include other agents conventional in the art having regard to the type of formulation in question, for example those suitable for oral administration may include flavoring agents.

As indicated, therapeutically effective amounts of the combinations of the invention (Compound $A^2$ in combination with Compound $B^2$) are administered to a human. Typically, the therapeutically effective amount of the administered agents of the present invention will depend upon a number of factors including, for example, the age and weight of the subject, the precise condition requiring treatment, the severity of the condition, the nature of the formulation, and the route of administration. Ultimately, the therapeutically effective amount will be at the discretion of the attending physician.

The combinations of the invention are tested for efficacy, advantageous and synergistic properties generally according to known procedures.

Suitably, the combinations of the inventions are tested for efficacy advantageous and synergistic properties generally according to the following tumor xenograft growth delay assays. Tumor cells are implanted subcutaneously or orthotopically in mice. When the tumor volume reaches 100-400 mm$^3$, mice are randomized to different treatment groups. Mice are treated with various doses of Compound A alone or in combination with various doses of Compound B, administered once or twice daily. Mice are weighed and tumors measured by calipers twice weekly. Tumor volumes are calculated using the formula: tumor volume=(Length×Width$^2$)/2. The percentage of tumor growth inhibition was calculated on each day of tumor measurement using the formula: 100× [1−(average growth of the compound-treated tumors/average growth of vehicle-treated control tumors)].

Alternatively, the combinations of the invention are tested for efficacy, advantageous and synergistic properties generally according to the following combination cell proliferation assays. Cells are plated in 384-well plates at 500 cells/well in culture media appropriate for each cell type, supplemented with 10% FBS and 1% penicillin/streptomycin, and incubated overnight at 37° C., 5% CO$_2$. Cells are treated in a grid manner with dilution of Compound A$^2$ (20 dilutions, including no compound, of 2-fold dilutions starting from 1-20 µM depending on combination) from left to right on 384-well plate and also treated with Compound B$^2$ (20 dilutions, including no compound, of 2-fold dilutions starting from 1-20 µM depending on combination) from top to bottom on 384-well plate and incubated as above for a further 72 hours. In some instances compounds are added in a staggered manner and incubation time can be extended up to 7 days. Cell growth is measured using CellTiter-Glo® reagent according to the manufacturer's protocol and signals are read on a PerkinElmer EnVision™ reader set for luminescence mode with a 0.5-second read. Data are analyzed as described below.

Results are expressed as a percentage of the t=0 value and plotted against compound(s) concentration. The t=0 value is normalized to 100% and represents the number of cells present at the time of compound addition. The cellular response is determined for each compound and/or compound combination using a 4- or 6-parameter curve fit of cell viability against concentration using the IDBS XLfit plug-in for Microsoft Excel software and determining the concentration required for 50% inhibition of cell growth (gIC$_{50}$). Background correction is made by subtraction of values from wells containing no cells. For each drug combination a Combination Index (CI), Excess Over Highest Single Agent (EOHSA) and Excess Over Bliss (EOBliss) are calculated according to known methods such as described in Chou and Talalay (1984) Advances in Enzyme Regulation, 22, 37 to 55; and Berenbaum, MC (1981) Adv. Cancer Research, 35, 269-335.

[Note: as used herein, when referring to the working example below and in FIG. 1 and only when referring to the working example below and in FIG. 1, Compound A is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate and Compound B is gemcitabine.]

In Vitro Cell Growth Inhibition by Compound A, Compound B (Gemcitabine), and their Combination in Pancreatic Tumor Cell Lines Methods:

Cell Lines and Growth Conditions

BxPC-3, HuP-T4, PL45, Panc-02-03, Mia-PaCa, HPAF-II, SW1990, Panc-08-13, Capan-1, AsPC-1, Capan-2, HPAC, YAPC and Panc-1 lines were used in the study. BxPC-3, Mia-PaCa, HPAF-11, SW1990, AsPC-1, Capan-2 and YAPC were cultured in RPMI 1640 medium (cat#72400 047, Invitrogen) containing 10% fetal bovine serum (FBS) (cat#SH30071.03, Hyclone). Capan-1 and HuP-T4 were cultured in RPMI 1640 medium containing 20% FBS. PL45 and PANC-1 lines were cultured in DMEM (ATCC 30-2002) containing 10% FBS. Panc-02-03 and Panc-08-13 were cultured in RPMI 1640 medium containing 15% fetal bovine serum and ITSX (51500-056, Gibco). HPAC was cultured in RPMI 1640 medium containing 5% FBS, ITSX, 40 ng/ml Hydrocortism, and 10 ng/ml EGF (85570C-1MG, SAFC Biosciences).

Cell Growth Inhibition Assay and Combination Data Analysis.

All cells were cultured for a minimum of 72 hours prior to cell plating. Cells were assayed in a 96-well tissue culture plate (NUNC 136102) of RPMI medium containing 10% FBS for all cells at 1,000 cells per well. Approximately 24 hours after plating, cells were exposed to ten, three-fold serial dilutions of compound or the combination of the two agents at a constant molar to molar ratio of 1:1 Compound A to Compound B in RPMI media containing 10% FBS. Cells were incubated in the presence of compounds for 3 days. ATP levels were determined by adding Cell Titer Glo® (Promega) according to the manufacturer's protocol. Briefly, Cell Titer Glo® was added to each plate, incubated for 30 minutes and then the luminescent signal was read on the SpectraMax L plate reader with a 0.5 sec integration time.

Inhibition of cell growth was estimated after treatment with compound or combination of compounds for three days and the signal was compared to cells treated with vehicle (DMSO). Cell growth was calculated relative to vehicle (DMSO) treated control wells. The concentration of compound that inhibits 50% of control cell growth (IC$_{50}$) was interpolated when y=50% of the vehicle control using non-linear regression with the equation, y=(A+(B−A)/(1+(C/x)^D))), where A is the minimum response (y$_{min}$), B is the maximum response (y$_{max}$), C is the inflection point of the curve (EC$_{50}$) and D is the Hill coefficient.

Combination effects on potency were evaluated using Combination Index (CI) which was calculated with the back-interpolated IC$_{50}$ values and the mutually non-exclusive equation derived by Chou and Talalay:

$$CI=Da/IC_{50}(a)+Db/IC_{50}(b)+(Da \times Db)/(IC_{50}(a) \times IC_{50}(b))$$

where IC$_{50}$(a) is the IC$_{50}$ of Compound A; IC$_{50}$(b) is the IC$_{50}$ for Compound B; Da is the concentration of Compound A in combination with Compound B that inhibited 50% of cell growth; and Db is the concentration of Compound B in combination with Compound A that inhibited 50% of cell growth. In general, a CI value <0.9, between 0.9 and 1.1, or >1.1 indicates synergy, additivity and antagonism, respectively. In general, the smaller the CI number, the greater is the strength of synergy.

The combination effects on the response scale were quantified by Excess Over Highest Single Agent (EOHSA) based on the concept of nonlinear blending as described in detail by Liu et al, 2011. EOHSA values are defined as increases in improvement (here, in 'percentage points' (ppts) difference) produced by the combination over the best single agent at its component dose level for the combination. For single agent and combination treatments, cells were exposed to compounds at a fixed-dose-ratio, and dose response curves were fit to the experimental data and analyzed using regression models. At specified total dose levels of IC$_{50}$ along the dose response curve, the dose combination (corresponding to IC$_{50}$) was determined for making EOHSA statistical inferences.

More specifically, for a combination drug experiment involving drug 1 at dose d1 and drug 2 at dose d2, (i.e., total dose equals d1+d2) is said to have a positive EOHSA if the mean response at the combination is better than the mean response to drug 1 at dose d1 or drug 2 at dose d2.

Results:

The effect of cell growth by a MEK1/2 inhibitor Compound A, gemcitabine Compound B, and the combination of the two compounds were determined in a panel of human pancreatic tumor cell lines. The mean $IC_{50}$s (from at least two independent experiments) and the combination effects at $IC_{50}$s are summarized in Table 1 with KRAS mutation status. BxPC3 cells with wild type KRAS were highly sensitive to both Compound A ($IC_{50}$=0.014 μM) and Compound B ($IC_{50}$=0.008 μM) as a single agent. The combination of Compound A and Compound B was slightly synergistic demonstrated by a CI value of 0.88 and enhanced cell growth inhibition determined by EOHSA analysis (15 ppts) in BxPC3 cells. KRAS mutant tumor lines, HuP-T4, PL45, Panc-02-03 and Mia-PaCa were sensitive to both Compound A with $IC_{50}$s ranging from 0.001 to 0.059 μM and Compound B with $IC_{50}$s ranging from 0.007 to 0.088 μM as a single agent. The combination of Compound A and Compound B showed synergistic to nearly additive effects with CI values from 0.55 to 0.93 in the four lines. Furthermore, KRAS mutant lines HPAF-11, SW1990, Panc-08-13 and Capan-1, which were moderately sensitive to compound A ($IC_{50}$s=0.059-0.193 μM), and insensitive to Compound B $IC_{50}$>1 μM), were more sensitive to the combination of Compound A and Compound B ($IC_{50}$s=0.003-0.012 μM). This combination also enhanced cell growth inhibition with EOHSAs from 11 to 23 ppts. In contrast, KRAS mutant lines AsPC-1, Capan-2, HPAC and YPAC were sensitive to either Compound A or Compound B alone, and showed combination activity similar to the most active single agent. KRAS mutant Panc-1 cells were resistant to both Compound A and Compound B, and showed moderate sensitivity to the combination of Compound A and Compound B.

Representative cell growth curves for BxPC-3, Panc-02-03, Mia-PaCa and Cagan-1 human pancreatic cancer cells are shown in FIG. 1.

Table 1. Cell growth inhibition by Compound A, Compound B and their combination in human pancreatic tumor cells.

TABLE 1

| Pancreatic cells | KRAS status | Compound A ($IC_{50}$, μM) | Compound B ($IC_{50}$, μM) | Compound A: Compound B = 1:1 ratio Compound A (+Compound B), ($IC_{50}$, μM) | Combination effects | |
|---|---|---|---|---|---|---|
| | | | | | CI | EOHSA (ppts) |
| BxPC-3 | WT | 0.014 ± 0.005 | 0.008 ± 0.001 | 0.004 ± 0.000 | 0.88 ± 0.27 | 15 ± 6 |
| HuP-T4 | G12V | 0.001 ± 0.001 | 0.007 ± 0.005 | 0.001 ± 0.001 | 0.93 ± 0.16 | 5 ± 3 |
| PL45 | G12D | 0.015 ± 0.004 | 0.013 ± 0.002 | 0.005 ± 0.001 | 0.80 ± 0.23 | 16 ± 8 |
| Panc-02-03 | G12D | 0.032 ± 0.013 | 0.088 ± 0.017 | 0.011 ± 0.003 | 0.62 ± 0.39 | 13 ± 8 |
| Mia-PaCa | G12C | 0.059 ± 0.028 | 0.021 ± 0.001 | 0.007 ± 0.001 | 0.55 ± 0.13 | 20 ± 3 |
| HPAF-II | G12D | 0.059 ± 0.053 | >1 | 0.012 ± 0.007 | n/a | 18 ± 3 |
| SW1990 | G12D | 0.062 ± 0.043 | ≥1 | 0.006 ± 0.003 | n/a | 23 ± 1 |
| Panc-08-13 | G12D | 0.067 ± 0.014 | >1 | 0.003 ± 0.001 | n/a | 11 ± 2 |
| Capan-1 | G12V | 0.193 ± 0.078 | >1 | 0.005 ± 0.001 | n/a | 20 ± 9 |
| AsPC-1 | G12D | 0.005 ± 0.000 | >1 | 0.005 ± 0.002 | n/a | 3 ± 9 |
| Capan-2 | G12V | 0.010 ± 0.001 | >1 | 0.017 ± 0.001 | n/a | −5 ± 0 |
| HPAC | G12D | 0.021 ± 0.006 | >1 | 0.013 ± 0.005 | n/a | 4 ± 2 |
| YAPC | G12V | >1 | 0.012 ± 0.008 | 0.009 ± 0.004 | n/a | 6 ± 9 |
| Panc-1 | G12D | >1 | >1 | 0.108 ± 0.001 | n/a | 22 ± 0 |

Table 1 Key:
$IC_{50}$: the concentration of Compound as single agent, or the concentration of Compound A or B in combination when Compound A and Compound B = 1:1 molar ratio that reduces cell growth by 50%;
CI; Combination Index;
n/a = not applicable
EOHSA: Excess over Highest Single Agent, measured as a percentage.

FIG. 1. Representative cell growth curves for BxPC-3, Panc-02-03, Mia-PaCa and Capan-1 human pancreatic cancer cells.

Reference List
(1) Chou T C, Talalay P. Quantitative analysis of dose-effect relationships: the combined effects of multiple drugs or enzyme inhibitors. Adv Enzyme Regul 1984; 22:27-55.
(2) Liu L, Shi H, Liu Y, Anderson A, Peterson J, Greger J, Martin A M, Gilmer T M. Synergistic effects of foretinib with HER-targeted agents in MET and HER1- or HER2-coactivated tumor cells. Mol Cancer Ther. 2011; 10(3): 518-30.

Because the combinations of the present invention are active in the above assays they exhibit advantageous therapeutic utility in treating cancer.

Suitably, the present invention relates to a method for treating or lessening the severity of breast cancer, including inflammatory breast cancer, ductal carcinoma, and lobular carcinoma.

Suitably the present invention relates to a method for treating or lessening the severity of colon cancer.

Suitably the present invention relates to a method for treating or lessening the severity of pancreatic cancer, including insulinomas, adenocarcinoma, ductal adenocarcinoma, adenosquamous carcinoma, acinar cell carcinoma, and glucagonoma.

Suitably the present invention relates to a method for treating or lessening the severity of skin cancer, including melanoma, including metastatic melanoma.

Suitably the present invention relates to a method for treating or lessening the severity of lung cancer including small cell lung cancer, non-small cell lung cancer, squamous cell carcinoma, adenocarcinoma, and large cell carcinoma.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably, the present invention relates to a method of treating or lessening the severity of a cancer that is either wild type or mutant for BRAF, KRAS, NRAS, HRAS, SOS1, NF1, or with activated receptor tyrosine kinases (e.g., EGFR, ErbB2, c-Kit, PDGFR, etc.). This includes patients who are wild type for each of, mutant for each of, and combinations of wild type and mutant of BRAF, KRAS, NRAS, HRAS, SOS1, NF1, and receptor tyrosine kinases (e.g., EGFR, ErbB2, c-Kit, PDGFR, etc.). The present invention also relates to a method of treating or lessening the severity of a cancer that has activated BRAF, KRAS, NRAS, HRAS, SOS1, NF1, or activated receptor tyrosine kinases (e.g., EGFR, ErbB2, c-Kit, PDGFR, etc.) .e.g., by mutation or amplification of the gene or overexpression of the protein.

The term "wild type" as is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Included in the term mutant is Single Nucleotide Polymorphism (SNP) where a single base pair distinction exists in the sequence of a nucleic acid strand compared to the most prevalently found (wild type) nucleic acid strand.

Cancers that are either wild type or mutant for BRAF, KRAS, NRAS, HRAS, SOS1, NF1, EGFR, ErbB2, c-Kit, or PDGFR, or have amplification or overexpression of BRAF, KRAS, NRAS, HRAS, NF1, EGFR, ErbB2, c-Kit, or PDGFR, are identified by known methods.

For example, wild type or mutant BRAF, KRAS, NRAS, HRAS, SOS1, NF1, EGFR, ErbB2, c-Kit, or PDGFR, tumor cells can be identified by DNA amplification and sequencing techniques, DNA and RNA detection techniques, including, but not limited to Northern and Southern blot, respectively, and/or various biochip and array technologies or in-situ hybridization. Wild type and mutant polypeptides can be detected by a variety of techniques including, but not limited to immunodiagnostic techniques such as ELISA, Western blot or immunocytochemistry.

This invention provides a combination comprising 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof.

This invention also provides for a combination comprising 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, for use in therapy.

This invention also provides for a combination comprising 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, for use in treating cancer.

This invention also provides a pharmaceutical composition comprising a combination of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof.

This invention also provides a combination kit comprising 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof.

This invention also provides for the use of a combination comprising 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, in the manufacture of a medicament.

This invention also provides for the use of a combination comprising 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, in the manufacture of a medicament to treat cancer.

This invention also provides a method of treating cancer which comprises administering a combination of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt, suitably the hydrochloride salt, thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, suitably the dimethyl sulfoxide solvate thereof, to a subject in need thereof.

The following examples are intended for illustration only and are not intended to limit the scope of the invention in any way.

EXPERIMENTAL DETAILS

Example 1

Capsule Composition

An oral dosage form for administering a combination of the present invention is produced by filling a standard two piece hard gelatin capsule with the ingredients in the proportions shown in Table I, below.

TABLE I

| INGREDIENTS | AMOUNTS |
| --- | --- |
| 4-amino-1-(2-deoxy-2,2-difluoro-β-D-erythro-pentofuranosyl)pyrimidin-2(1H)-on 2',2'-difluoro-2'-deoxycytidine hydrochloride (Compound A) | 1000 mg |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 2 mg |
| Mannitol | 250 mg |
| Talc | 125 mg |
| Magnesium Stearate | 8 mg |

Example 2

Capsule Composition

An oral dosage form for administering one of the compounds of the present invention is produced by filing a standard two piece hard gelatin capsule with the ingredients in the proportions shown in Table II, below.

TABLE II

| INGREDIENTS | AMOUNTS |
| --- | --- |
| 4-amino-1-(2-deoxy-2,2-difluoro-β-D-erythro-pentofuranosyl)pyrimidin-2(1H)-on 2',2'-difluoro-2'-deoxycytidine hydrochloride (Compound A) | 1000 mg |
| Mannitol | 150 mg |
| Talc | 16 mg |
| Magnesium Stearate | 4 mg |

Example 3

Capsule Composition

An oral dosage form for administering one of the compounds of the present invention is produced by filing a standard two piece hard gelatin capsule with the ingredients in the proportions shown in Table III, below.

TABLE III

| INGREDIENTS | AMOUNTS |
| --- | --- |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 2 mg |
| Mannitol | 150 mg |

TABLE III-continued

| INGREDIENTS | AMOUNTS |
| --- | --- |
| Talc | 12 mg |
| Magnesium Stearate | 8 mg |

Example 4

Tablet Composition

The sucrose, microcrystalline cellulose and the compounds of the invented combination, as shown in Table IV below, are mixed and granulated in the proportions shown with a 10% gelatin solution. The wet granules are screened, dried, mixed with the starch, talc and stearic acid, then screened and compressed into a tablet.

TABLE IV

| INGREDIENTS | AMOUNTS |
| --- | --- |
| 4-amino-1-(2-deoxy-2,2-difluoro-β-D-erythro-pentofuranosyl)pyrimidin-2(1H)-on 2',2'-difluoro-2'-deoxycytidine hydrochloride (the hydrochloride salt of Compound A) | 1000 mg |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 5 mg |
| Microcrystalline cellulose | 300 mg |
| sucrose | 10 mg |
| starch | 40 mg |
| talc | 20 mg |
| stearic acid | 5 mg |

Example 5

Tablet Composition

The sucrose, microcrystalline cellulose and one of the compounds of the invented combination, as shown in Table V below, are mixed and granulated in the proportions shown with a 10% gelatin solution. The wet granules are screened, dried, mixed with the starch, talc and stearic acid, then screened and compressed into a tablet.

TABLE V

| INGREDIENTS | AMOUNTS |
| --- | --- |
| 4-amino-1-(2-deoxy-2,2-difluoro-β-D-erythro-pentofuranosyl)pyrimidin-2(1H)-on 2',2'-difluoro-2'-deoxycytidine hydrochloride (the hydrochloride salt of Compound A) | 1000 mg |
| Microcrystalline cellulose | 200 mg |
| sucrose | 4 mg |
| starch | 2 mg |
| talc | 1 mg |
| stearic acid | 0.5 mg |

Example 6

Tablet Composition

The sucrose, microcrystalline cellulose and one of the compounds of the invented combination, as shown in Table VI below, are mixed and granulated in the proportions shown with a 10% gelatin solution. The wet granules are screened, dried, mixed with the starch, talc and stearic acid, then screened and compressed into a tablet.

TABLE VI

| INGREDIENTS | AMOUNTS |
| --- | --- |
| N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide (the dimethyl sulfoxide solvate of Compound B) | 2 mg |
| Microcrystalline cellulose | 300 mg |
| sucrose | 40 mg |
| starch | 20 mg |
| talc | 10 mg |
| stearic acid | 5 mg |

Example 7

Injectable Parenteral Composition

An injectable form for administering a compound of the presently invented combination is produced by stirring 1.5% by weight of 4-amino-1-(2-deoxy-2,2-difluoro-β-D-erythro-pentofuranosyl)pyrimidin-2(1H)-on 2',2'-difluoro-2'-deoxycytidine hydrochloride (the hydrochloride salt of Compound A) in 10% by volume propylene glycol in water. Suitably to administer a dose providing 1000 mg/m2 intravenous of Compound A.

While the preferred embodiments of the invention are illustrated by the above, it is to be understood that the invention is not limited to the precise instructions herein disclosed and that the right to all modifications coming within the scope of the following claims is reserved.

We claim:
1. A combination comprising:
   (i) a compound of Structure (I):

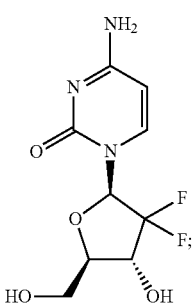

(I)

or a pharmaceutically acceptable salt thereof; and
   (ii) a compound of Structure (II):

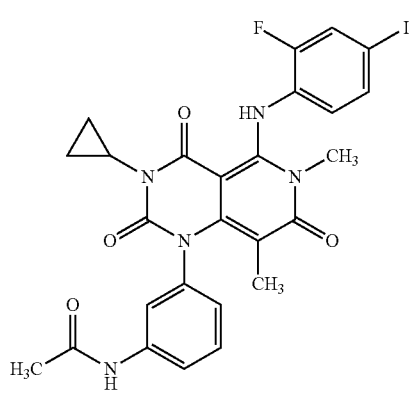

(II)

or a pharmaceutically acceptable salt or solvate thereof.

2. A combination according to claim 1 where the compound of Structure (I) is in the form of a hydrochloride salt and the compound of Structure (II) is in the form of a dimethyl sulfoxide solvate.

3. A kit comprising a combination according to claim 1 together with a pharmaceutically acceptable carrier or carriers.

4. A combination according to claim 1 where the amount of the compound of Structure (I) is 1000 mg/m2 administered over a period of 30 minutes, and the amount of the compound of Structure (II) is an amount selected from: about 0.5 mg, 1 mg and 2 mg, and that amount is administered once per day.

5. A method of treating cancer in a human in need thereof which comprises the in vivo administration of a therapeutically effective amount of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, to such human,
   wherein the combination is administered within a specified period, and
   wherein the combination is administered for a duration of time.

6. A method according to claim 5 which comprises the in vivo administration of 4-amino-1-(2-deoxy-2,2-difluoro-β-D-erythro-pentofuranosyl)pyrimidin-2(1H)-on 2',2'-difluoro-2'-deoxycytidine hydrochloride, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide dimethyl sulfoxide;
   wherein the administration protocol is:
   4-amino-1-(2-deoxy-2,2-difluoro-β-D-erythro-pentofuranosyl)pyrimidin-2(1H)-on 2',2'-difluoro-2'-deoxycytidine hydrochloride administered in:
      a first cycle consisting of 1000 mg/m2 intravenous infusion over 30 minutes weekly for 7 weeks followed by one week of no treatment with Compound A,
      with
      subsequent cycles consisting of 1000 mg/m2 intravenous infusion over 30 minutes on days 1, 8, and 15 followed by 1 week of no treatment with Compound A for each 28-day treatment period;
   and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl} acetamide dimethyl sulfoxide administered in:
      a daily dose selected from: about 0.5 mg, about 1 mg and about 2 mg, suitably about 2 mg, by weight of the un-solvated compound.

7. A method according to claim 6 wherein the cancer is selected from:
   breast cancer, inflammatory breast cancer, ductal carcinoma, lobular carcinoma, colon cancer, pancreatic cancer, insulinoma, adenocarcinoma, ductal adenocarcinoma, adenosquamous carcinoma, acinar cell carcinoma, glucagonoma, melanoma, metastatic melanoma, lung cancer, small cell lung cancer, non-small cell lung cancer, squamous cell carcinoma, adenocarcinoma, and large cell carcinoma, brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

8. A method according to claim 7 wherein the cancer selected from ovarian, breast, pancreatic and prostate.

9. A method of treating or lessening the severity of cancer that is either wild type or mutant for BRAF, KRAS, NRAS, HRAS, SOS1, NF1, EGFR, ErbB2, c-Kit, PDGFR, or ErbB-2 genes or have overexpression of EGFR or ErbB2 protein, in a human in need thereof which comprises the in vivo administration of a therapeutically effective amount of 4-amino-1-(2-deoxy-2,2-difluoro-β-D-erythro-pentofuranosyl)pyrimidin-2(1H)-on 2',2'-difluoro-2'-deoxycytidine, or a pharmaceutically acceptable salt thereof, and N-{3-[3-cyclopropyl-5-(2-fluoro-4-iodo-phenylamino)6,8-dimethy;-2,4,7-trioxo-3,4,6,7-tetrahydro-2H-pyrido[4,3-d]pyrimidin-1-yl]phenyl}acetamide, or a pharmaceutically acceptable salt or solvate thereof, to such human, wherein the combination is administered within a specified period, and wherein the combination is administered for a duration of time.

10. A method according to claim 9 wherein the cancer selected from ovarian, breast, pancreatic and prostate.

* * * * *